(12) United States Patent
Pimenta et al.

(10) Patent No.: US 8,287,597 B1
(45) Date of Patent: Oct. 16, 2012

(54) METHOD AND APPARATUS FOR PERFORMING SPINE SURGERY

(75) Inventors: Luiz Pimenta, Sao Paulo (BR); Andrew Morris, San Diego, CA (US); Brian Snider, San Diego, CA (US); Michael Serra, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 115 days.

(21) Appl. No.: 12/799,021

(22) Filed: Apr. 16, 2010

Related U.S. Application Data

(60) Provisional application No. 61/212,921, filed on Apr. 16, 2009, provisional application No. 61/319,823, filed on Mar. 31, 2010.

(51) Int. Cl.
*A61F 2/44* (2006.01)
(52) U.S. Cl. .................................................. 623/17.16
(58) Field of Classification Search ..... 623/17.11–17.16
See application file for complete search history.

(56) References Cited

U.S. PATENT DOCUMENTS

| | | | |
|---|---|---|---|
| 208,227 A | 9/1878 | Dorr | |
| 972,983 A | 10/1910 | Arthur | |
| 1,328,624 A | 1/1920 | Graham | |
| 1,548,184 A | 8/1925 | Cameron | |
| 2,704,064 A | 6/1955 | Fizzell et al. | |
| 2,736,002 A | 2/1956 | Oriel | |
| 2,808,826 A | 10/1957 | Reiner et al. | |
| 3,364,929 A | 1/1968 | Ide et al. | |
| 3,486,505 A | 12/1969 | Morrison | |
| 3,518,993 A | 7/1970 | Blake | |
| 3,604,487 A | 9/1971 | Gilbert | |
| 3,664,329 A | 5/1972 | Naylor | |
| 3,682,162 A | 8/1972 | Colyer | |
| 3,745,995 A | 7/1973 | Kraus | |
| 3,785,368 A | 1/1974 | McCarthy et al. | |
| 3,830,226 A | 8/1974 | Staub et al. | |
| 3,848,601 A | 11/1974 | Ma et al. | |
| 3,867,728 A * | 2/1975 | Stubstad et al. ........... | 623/17.16 |
| 3,957,036 A | 5/1976 | Normann | |
| 4,026,304 A | 5/1977 | Levy | |
| 4,026,305 A | 5/1977 | Brownlee et al. | |
| 4,099,519 A | 7/1978 | Warren | |
| 4,164,214 A | 8/1979 | Stark et al. | |
| 4,207,897 A | 6/1980 | Lloyd et al. | |
| 4,224,949 A | 9/1980 | Scott et al. | |
| 4,226,228 A | 10/1980 | Shin et al. | |

(Continued)

FOREIGN PATENT DOCUMENTS

CA 2015507 1/1999

(Continued)

OTHER PUBLICATIONS

Anatomy of the Lumbar Spine in MED TM MicroEndoscopic Discectomy (1997 Ludann Grand Rapids MI), 14 pgs.

(Continued)

*Primary Examiner* — Alvin Stewart
*Assistant Examiner* — James Palmer
(74) *Attorney, Agent, or Firm* — Jonathan Spangler; Rory Schermerhorn

(57) ABSTRACT

Systems and methods are described for correcting sagittal imbalance in a spine including instruments for performing the controlled release of the anterior longitudinal ligament through a lateral access corridor and hyper-lordotic lateral implants.

20 Claims, 7 Drawing Sheets

U.S. PATENT DOCUMENTS

| | | |
|---|---|---|
| 4,235,242 A | 11/1980 | Howson et al. |
| 4,285,347 A | 8/1981 | Hess |
| 4,291,705 A | 9/1981 | Severinghaus et al. |
| 4,461,300 A | 7/1984 | Christensen |
| 4,501,269 A | 2/1985 | Bagby |
| 4,515,168 A | 5/1985 | Chester et al. |
| 4,519,403 A | 5/1985 | Dickhudt |
| 4,545,374 A | 10/1985 | Jacobson |
| 4,561,445 A | 12/1985 | Berke et al. |
| 4,562,832 A | 1/1986 | Wilder et al. |
| 4,573,448 A | 3/1986 | Kambin |
| 4,592,369 A | 6/1986 | Davis et al. |
| 4,595,018 A | 6/1986 | Rantala |
| 4,611,597 A | 9/1986 | Kraus |
| 4,633,889 A | 1/1987 | Talalla |
| 4,646,738 A | 3/1987 | Trott |
| 4,657,550 A | 4/1987 | Daher |
| 4,658,835 A | 4/1987 | Pohndorf |
| 4,743,256 A | 5/1988 | Brantigan |
| 4,744,371 A | 5/1988 | Harris |
| 4,759,377 A | 7/1988 | Dykstra |
| 4,781,591 A | 11/1988 | Allen |
| 4,784,150 A | 11/1988 | Voorhies et al. |
| 4,807,642 A | 2/1989 | Brown |
| 4,834,757 A | 5/1989 | Brantigan |
| 4,877,020 A | 10/1989 | Vich |
| 4,878,915 A | 11/1989 | Brantigan |
| 4,892,105 A | 1/1990 | Prass |
| 4,913,134 A | 4/1990 | Luque |
| 4,926,865 A | 5/1990 | Oman |
| 4,932,975 A | 6/1990 | Main et al. |
| 4,950,296 A | 8/1990 | McIntyre |
| 4,961,740 A | 10/1990 | Ray et al. |
| 4,962,766 A | 10/1990 | Herzon |
| 4,964,411 A | 10/1990 | Johnson et al. |
| 5,007,902 A | 4/1991 | Witt |
| 5,015,247 A | 5/1991 | Michelson |
| 5,026,373 A | 6/1991 | Ray et al. |
| 5,047,055 A | 9/1991 | Bao et al. |
| 5,052,373 A | 10/1991 | Michelson |
| 5,055,104 A | 10/1991 | Ray |
| 5,058,602 A | 10/1991 | Brody |
| 5,062,845 A | 11/1991 | Kuslich et al. |
| 5,071,437 A | 12/1991 | Steffee |
| 5,081,990 A | 1/1992 | Deletis |
| 5,092,344 A | 3/1992 | Lee |
| 5,092,572 A | 3/1992 | Litwak et al. |
| 5,127,403 A | 7/1992 | Brownlee |
| 5,133,717 A | 7/1992 | Chopin |
| 5,133,755 A | 7/1992 | Brekke |
| 5,161,533 A | 11/1992 | Prass et al. |
| 5,171,278 A | 12/1992 | Pisharodi |
| 5,171,279 A | 12/1992 | Mathews |
| 5,192,327 A | 3/1993 | Brantigan |
| 5,195,541 A | 3/1993 | Obenchain |
| 5,196,015 A | 3/1993 | Neubardt |
| 5,217,497 A | 6/1993 | Mehdian |
| RE34,390 E | 9/1993 | Culver |
| 5,255,691 A | 10/1993 | Otten |
| 5,263,953 A | 11/1993 | Bagby |
| 5,269,785 A | 12/1993 | Bonutti |
| 5,282,468 A | 2/1994 | Klepinski |
| 5,284,153 A | 2/1994 | Raymond et al. |
| 5,284,154 A | 2/1994 | Raymond et al. |
| 5,290,494 A | 3/1994 | Coombes et al. |
| 5,295,994 A | 3/1994 | Bonutti |
| 5,299,563 A | 4/1994 | Seton |
| 5,300,076 A | 4/1994 | Lerich |
| 5,304,210 A | 4/1994 | Crook |
| 5,306,307 A | 4/1994 | Senter et al. |
| 5,306,309 A | 4/1994 | Wagner et al. |
| 5,312,417 A | 5/1994 | Wilk |
| 5,313,956 A | 5/1994 | Knutsson et al. |
| 5,313,962 A | 5/1994 | Obenchain |
| 5,322,505 A | 6/1994 | Krause et al. |
| 5,327,902 A | 7/1994 | Lemmen |
| 5,331,975 A | 7/1994 | Bonutti |
| 5,333,618 A | 8/1994 | Lekhtman et al. |
| 5,334,205 A | 8/1994 | Cain |
| 5,336,223 A | 8/1994 | Rogers |
| 5,342,384 A | 8/1994 | Sugarbaker |
| 5,364,400 A | 11/1994 | Rego, Jr. et al. |
| 5,375,067 A | 12/1994 | Berchin |
| 5,375,594 A | 12/1994 | Cueva |
| 5,383,876 A | 1/1995 | Nardella |
| 5,395,317 A | 3/1995 | Kambin |
| 5,395,372 A | 3/1995 | Holt et al. |
| 5,397,363 A | 3/1995 | Gelbard |
| 5,397,364 A | 3/1995 | Kozak |
| 5,405,391 A | 4/1995 | Henderson et al. |
| 5,413,602 A | 5/1995 | Metz-Stavenhagen |
| 5,425,772 A | 6/1995 | Brantigan |
| 5,431,658 A | 7/1995 | Moskovich |
| 5,443,514 A | 8/1995 | Steffee |
| 5,443,515 A | 8/1995 | Cohen et al. |
| 5,445,639 A | 8/1995 | Kuslich et al. |
| 5,450,845 A | 9/1995 | Axelgaard |
| 5,454,811 A | 10/1995 | Huebner |
| 5,458,638 A | 10/1995 | Kuslich et al. |
| 5,474,057 A | 12/1995 | Makower et al. |
| 5,474,558 A | 12/1995 | Neubardt |
| 5,480,440 A | 1/1996 | Kambin |
| 5,482,038 A | 1/1996 | Ruff |
| 5,484,403 A | 1/1996 | Yoakum et al. |
| 5,484,437 A | 1/1996 | Michelson |
| 5,489,307 A | 2/1996 | Kuslich et al. |
| 5,489,308 A | 2/1996 | Kuslich et al. |
| 5,509,893 A | 4/1996 | Pracas |
| 5,514,153 A | 5/1996 | Bonutti |
| 5,514,180 A | 5/1996 | Heggeness et al. |
| 5,522,879 A | 6/1996 | Scopelianos |
| 5,522,899 A | 6/1996 | Michelson |
| 5,524,624 A | 6/1996 | Tepper et al. |
| 5,527,312 A | 6/1996 | Ray |
| 5,534,030 A | 7/1996 | Navarro et al. |
| 5,540,235 A | 7/1996 | Wilson |
| 5,540,688 A | 7/1996 | Navas |
| 5,545,222 A | 8/1996 | Bonutti |
| 5,549,656 A | 8/1996 | Reiss |
| 5,560,372 A | 10/1996 | Cory |
| 5,562,736 A | 10/1996 | Ray et al. |
| 5,565,005 A | 10/1996 | Erickson et al. |
| 5,566,678 A | 10/1996 | Cadwell |
| 5,571,149 A | 11/1996 | Liss et al. |
| 5,571,190 A | 11/1996 | Ulrich |
| 5,571,192 A | 11/1996 | Schonhoffer |
| 5,579,781 A | 12/1996 | Cooke |
| 5,593,409 A | 1/1997 | Michelson |
| 5,593,429 A | 1/1997 | Ruff |
| 5,599,279 A | 2/1997 | Slotman et al. |
| 5,609,636 A | 3/1997 | Kohrs et al. |
| 5,611,800 A | 3/1997 | Davis et al. |
| 5,611,810 A | 3/1997 | Arnold et al. |
| 5,630,813 A | 5/1997 | Kieturakis |
| 5,632,747 A | 5/1997 | Scarborough et al. |
| 5,645,598 A | 7/1997 | Brosnahan et al. |
| 5,653,761 A | 8/1997 | Pisharodi |
| 5,653,762 A | 8/1997 | Pisharodi |
| 5,658,336 A | 8/1997 | Pisharodi |
| 5,658,337 A | 8/1997 | Kohrs et al. |
| 5,662,710 A | 9/1997 | Bonutti |
| 5,665,122 A | 9/1997 | Kambin |
| 5,667,508 A | 9/1997 | Errico et al. |
| 5,669,909 A | 9/1997 | Zdeblick et al. |
| 5,671,752 A | 9/1997 | Sinderby et al. |
| 5,676,703 A | 10/1997 | Gelbard |
| 5,681,265 A | 10/1997 | Maeda et al. |
| 5,683,394 A | 11/1997 | Rinner |
| 5,683,400 A | 11/1997 | McGuire |
| 5,683,464 A | 11/1997 | Wagner et al. |
| 5,690,629 A | 11/1997 | Asher et al. |
| 5,700,264 A | 12/1997 | Zucherman et al. |
| 5,700,291 A | 12/1997 | Kuslich et al. |
| 5,700,292 A | 12/1997 | Margulies |
| 5,702,449 A | 12/1997 | McKay |
| 5,702,451 A | 12/1997 | Biedermann et al. |
| 5,702,453 A | 12/1997 | Rabbe et al. |

| Patent | Date | Inventor |
|---|---|---|
| 5,702,454 A | 12/1997 | Baumgartner |
| 5,702,455 A | 12/1997 | Saggar |
| 5,703,451 A | 12/1997 | Yamamichi |
| 5,707,359 A | 1/1998 | Bufalini |
| 5,707,373 A | 1/1998 | Sevrain et al. |
| 5,711,307 A | 1/1998 | Smits |
| 5,711,957 A | 1/1998 | Patat et al. |
| 5,716,415 A | 2/1998 | Steffee |
| 5,720,748 A | 2/1998 | Kuslich et al. |
| 5,720,751 A | 2/1998 | Jackson |
| 5,728,046 A | 3/1998 | Mayer et al. |
| 5,728,159 A | 3/1998 | Stroever et al. |
| 5,741,253 A | 4/1998 | Michelson |
| 5,741,261 A | 4/1998 | Moskovitz et al. |
| 5,755,797 A | 5/1998 | Baumgartner |
| 5,759,159 A | 6/1998 | Masreliez |
| 5,762,629 A | 6/1998 | Kambin |
| 5,766,252 A | 6/1998 | Henry et al. |
| 5,772,661 A | 6/1998 | Michelson |
| 5,775,331 A | 7/1998 | Raymond et al. |
| 5,775,797 A | 7/1998 | Henstra |
| 5,776,144 A | 7/1998 | Leysieffer et al. |
| 5,779,642 A | 7/1998 | Nightengale |
| 5,782,830 A | 7/1998 | Farris |
| 5,782,919 A | 7/1998 | Zdeblick et al. |
| 5,785,658 A | 7/1998 | Benaron |
| 5,785,710 A | 7/1998 | Michelson |
| 5,792,044 A | 8/1998 | Foley et al. |
| 5,797,854 A | 8/1998 | Hedgecock |
| 5,797,909 A | 8/1998 | Michelson |
| 5,800,549 A | 9/1998 | Bao et al. |
| 5,800,550 A | 9/1998 | Sertich |
| 5,814,073 A | 9/1998 | Bonutti |
| 5,814,084 A | 9/1998 | Grivas et al. |
| 5,830,151 A | 11/1998 | Hadzic et al. |
| 5,851,191 A | 12/1998 | Gozani |
| 5,851,208 A | 12/1998 | Trott |
| 5,853,373 A | 12/1998 | Griffith et al. |
| 5,860,973 A | 1/1999 | Michelson |
| 5,862,314 A | 1/1999 | Jeddeloh |
| 5,865,845 A | 2/1999 | Thalgott |
| 5,865,848 A | 2/1999 | Baker |
| 5,872,314 A | 2/1999 | Clinton |
| 5,885,210 A | 3/1999 | Cox |
| 5,885,219 A | 3/1999 | Nightengale |
| 5,885,299 A | 3/1999 | Winslow et al. |
| 5,888,196 A | 3/1999 | Bonutti |
| 5,888,219 A | 3/1999 | Bonutti |
| 5,888,224 A | 3/1999 | Beckers et al. |
| 5,891,147 A | 4/1999 | Moskovitz et al. |
| 5,893,890 A | 4/1999 | Pisharodi |
| 5,902,231 A | 5/1999 | Foley et al. |
| 5,904,719 A | 5/1999 | Errico et al. |
| 5,910,315 A | 6/1999 | Stevenson et al. |
| 5,928,139 A | 7/1999 | Koros et al. |
| 5,928,158 A | 7/1999 | Aristides |
| 5,931,777 A | 8/1999 | Sava |
| 5,935,131 A | 8/1999 | Bonutti et al. |
| 5,938,688 A | 8/1999 | Schiff |
| 5,942,698 A | 8/1999 | Stevens |
| 5,944,658 A | 8/1999 | Koros et al. |
| 5,954,769 A | 9/1999 | Rosenlicht |
| 5,968,098 A | 10/1999 | Winslow |
| 5,976,094 A | 11/1999 | Gozani et al. |
| 5,993,474 A | 11/1999 | Ouchi |
| 6,003,426 A | 12/1999 | Kobayashi et al. |
| 6,004,262 A | 12/1999 | Putz et al. |
| 6,004,312 A | 12/1999 | Finneran |
| 6,004,326 A | 12/1999 | Castro et al. |
| 6,007,487 A | 12/1999 | Foley et al. |
| 6,008,433 A | 12/1999 | Stone |
| 6,015,436 A | 1/2000 | Schunhuffer |
| 6,024,696 A | 2/2000 | Hoftman et al. |
| 6,027,456 A | 2/2000 | Feler et al. |
| 6,033,405 A | 3/2000 | Winslow et al. |
| 6,038,469 A | 3/2000 | Karlsson et al. |
| 6,038,477 A | 3/2000 | Kayyali |
| 6,039,761 A | 3/2000 | Li et al. |
| 6,042,582 A | 3/2000 | Ray |
| 6,045,580 A | 4/2000 | Scarborough et al. |
| 6,048,342 A | 4/2000 | Zucherman et al. |
| 6,050,992 A | 4/2000 | Nichols |
| 6,059,829 A | 5/2000 | Schlapfer et al. |
| 6,063,088 A | 5/2000 | Winslow |
| 6,074,343 A | 6/2000 | Nathanson et al. |
| 6,083,154 A | 7/2000 | Liu et al. |
| 6,083,225 A | 7/2000 | Winslow et al. |
| 6,095,987 A | 8/2000 | Shmulewitz |
| 6,096,080 A | 8/2000 | Nicholson et al. |
| 6,102,948 A | 8/2000 | Brosnahan, III |
| 6,104,957 A | 8/2000 | Alo et al. |
| 6,104,960 A | 8/2000 | Duysens et al. |
| 6,120,503 A | 9/2000 | Michelson |
| 6,120,506 A | 9/2000 | Kohrs et al. |
| 6,126,660 A | 10/2000 | Dietz |
| 6,132,386 A | 10/2000 | Gozani et al. |
| 6,132,387 A | 10/2000 | Gozani et al. |
| 6,132,472 A | 10/2000 | Bonutti |
| 6,135,965 A | 10/2000 | Tumer et al. |
| 6,139,493 A | 10/2000 | Koros et al. |
| 6,143,033 A | 11/2000 | Paul et al. |
| 6,146,335 A | 11/2000 | Gozani |
| 6,152,871 A | 11/2000 | Foley et al. |
| 6,159,211 A | 12/2000 | Boriani et al. |
| 6,159,215 A | 12/2000 | Urbahns et al. |
| 6,161,047 A | 12/2000 | King et al. |
| 6,174,311 B1 | 1/2001 | Branch et al. |
| 6,181,961 B1 | 1/2001 | Prass |
| 6,193,756 B1 | 2/2001 | Studer et al. |
| 6,196,969 B1 | 3/2001 | Bester et al. |
| 6,200,347 B1 | 3/2001 | Anderson |
| 6,206,826 B1 | 3/2001 | Mathews et al. |
| 6,217,509 B1 | 4/2001 | Foley et al. |
| 6,224,549 B1 | 5/2001 | Drongelen |
| 6,224,607 B1 | 5/2001 | Michelson |
| 6,224,631 B1 | 5/2001 | Kohrs |
| 6,241,769 B1 | 6/2001 | Nicholson et al. |
| 6,241,771 B1 | 6/2001 | Gresser et al. |
| 6,251,140 B1 | 6/2001 | Marino et al. |
| 6,258,125 B1 | 7/2001 | Paul et al. |
| 6,259,945 B1 | 7/2001 | Epstein et al. |
| 6,264,651 B1 | 7/2001 | Underwood et al. |
| 6,266,558 B1 | 7/2001 | Gozani et al. |
| 6,273,905 B1 | 8/2001 | Streeter |
| 6,277,149 B1 | 8/2001 | Boyle et al. |
| 6,292,701 B1 | 9/2001 | Prass et al. |
| 6,306,100 B1 | 10/2001 | Prass |
| 6,308,712 B1 | 10/2001 | Shaw |
| 6,312,392 B1 | 11/2001 | Herzon |
| 6,319,257 B1 | 11/2001 | Carignan et al. |
| 6,325,764 B1 | 12/2001 | Griffith et al. |
| 6,334,068 B1 | 12/2001 | Hacker |
| 6,348,058 B1 | 2/2002 | Melkent et al. |
| 6,360,750 B1 | 3/2002 | Gerber et al. |
| 6,371,968 B1 | 4/2002 | Kogasaka et al. |
| 6,371,989 B1 | 4/2002 | Chauvin et al. |
| 6,383,221 B1 | 5/2002 | Scarborough et al. |
| 6,409,766 B1 | 6/2002 | Brett |
| 6,425,772 B1 | 7/2002 | Bernier et al. |
| 6,425,859 B1 | 7/2002 | Foley et al. |
| 6,425,901 B1 | 7/2002 | Zhu et al. |
| 6,432,140 B1 | 8/2002 | Lin |
| 6,440,142 B1 | 8/2002 | Ralph et al. |
| 6,442,814 B1 | 9/2002 | Landry et al. |
| 6,447,547 B1 | 9/2002 | Michelson |
| 6,450,952 B1 | 9/2002 | Rioux et al. |
| 6,451,015 B1 | 9/2002 | Rittman, III et al. |
| 6,454,806 B1 | 9/2002 | Cohen et al. |
| 6,466,817 B1 | 10/2002 | Kaula et al. |
| 6,468,205 B1 | 10/2002 | Mollenauer et al. |
| 6,468,207 B1 | 10/2002 | Fowler, Jr. |
| 6,468,311 B2 | 10/2002 | Boyd et al. |
| 6,491,724 B1 | 12/2002 | Ferree |
| 6,500,128 B2 | 12/2002 | Marino |
| 6,520,907 B1 | 2/2003 | Foley et al. |
| 6,524,320 B2 | 2/2003 | DiPoto |
| 6,527,773 B1 | 3/2003 | Lin et al. |
| 6,535,759 B1 | 3/2003 | Epstein et al. |

| | | | | | | |
|---|---|---|---|---|---|---|
| D472,634 S | 4/2003 | Anderson | | 2003/0105528 A1 | 6/2003 | Shimp et al. |
| D473,650 S | 4/2003 | Anderson | | 2003/0139648 A1 | 7/2003 | Foley et al. |
| 6,547,823 B2 | 4/2003 | Scarborough et al. | | 2003/0139812 A1 | 7/2003 | Garcia et al. |
| 6,558,423 B1 * | 5/2003 | Michelson ............... 623/17.11 | | 2003/0149341 A1 | 8/2003 | Clifton |
| 6,564,078 B1 | 5/2003 | Marino et al. | | 2003/0225405 A1 | 12/2003 | Weiner |
| 6,579,244 B2 | 6/2003 | Goodwin | | 2003/0236544 A1 | 12/2003 | Lunsford et al. |
| 6,595,998 B2 | 7/2003 | Johnson et al. | | 2004/0153155 A1 | 8/2004 | Chung et al. |
| 6,620,157 B1 | 9/2003 | Dabney et al. | | 2004/0199084 A1 | 10/2004 | Kelleher et al. |
| 6,626,905 B1 | 9/2003 | Schmiel et al. | | 2004/0225228 A1 | 11/2004 | Ferree |
| 6,635,086 B2 | 10/2003 | Lin | | 2005/0004593 A1 | 1/2005 | Simonson |
| 6,645,194 B2 | 11/2003 | Briscoe et al. | | 2005/0004623 A1 | 1/2005 | Miles et al. |
| 6,648,895 B2 | 11/2003 | Burkus et al. | | 2005/0033380 A1 | 2/2005 | Tanner et al. |
| 6,672,019 B1 | 1/2004 | Wenz | | 2005/0075578 A1 | 4/2005 | Gharib et al. |
| 6,676,703 B2 | 1/2004 | Biscup | | 2005/0080320 A1 | 4/2005 | Lee et al. |
| 6,679,833 B2 | 1/2004 | Smith et al. | | 2005/0149035 A1 | 7/2005 | Pimenta et al. |
| 6,706,067 B2 | 3/2004 | Shimp et al. | | 2005/0182454 A1 | 8/2005 | Gharib et al. |
| 6,719,692 B2 | 4/2004 | Kleffner et al. | | 2005/0192575 A1 | 9/2005 | Pacheco |
| 6,743,255 B2 | 6/2004 | Ferree | | 2005/0197702 A1 | 9/2005 | Coppes et al. |
| 6,746,484 B1 | 6/2004 | Liu et al. | | 2006/0025703 A1 | 2/2006 | Miles et al. |
| 6,755,841 B2 | 6/2004 | Fraser et al. | | 2006/0052828 A1 | 3/2006 | Kim et al. |
| 6,760,616 B2 | 7/2004 | Hoey et al. | | 2006/0069315 A1 | 3/2006 | Miles et al. |
| 6,761,739 B2 | 7/2004 | Shepard | | 2006/0129244 A1 * | 6/2006 | Ensign ............... 623/17.16 |
| 6,770,074 B2 | 8/2004 | Michelson | | 2006/0224078 A1 | 10/2006 | Hoey et al. |
| 6,796,985 B2 | 9/2004 | Bolger et al. | | 2007/0016097 A1 | 1/2007 | Farquhar et al. |
| 6,810,281 B2 | 10/2004 | Brock et al. | | 2007/0191945 A1 | 8/2007 | Yu et al. |
| 6,819,956 B2 | 11/2004 | DiLorenzo | | 2007/0198062 A1 | 8/2007 | Miles et al. |
| 6,824,564 B2 | 11/2004 | Crozet | | 2007/0270972 A1 * | 11/2007 | Gordon et al. ............... 623/17.16 |
| 6,847,849 B2 | 1/2005 | Mamo et al. | | 2007/0293782 A1 | 12/2007 | Marino |
| 6,849,047 B2 | 2/2005 | Goodwin | | 2008/0058606 A1 | 3/2008 | Miles et al. |
| 6,855,105 B2 | 2/2005 | Jackson, III et al. | | 2008/0064976 A1 | 3/2008 | Kelleher et al. |
| 6,871,099 B1 | 3/2005 | Whitehurst et al. | | 2008/0064977 A1 | 3/2008 | Kelleher et al. |
| D503,801 S | 4/2005 | Jackson | | 2008/0065178 A1 | 3/2008 | Kelleher et al. |
| 6,902,569 B2 | 6/2005 | Parmer et al. | | 2008/0071191 A1 | 3/2008 | Kelleher et al. |
| 6,923,814 B1 | 8/2005 | Hildebrand et al. | | 2008/0097164 A1 | 4/2008 | Miles et al. |
| 6,926,728 B2 | 8/2005 | Zucherman et al. | | 2008/0300465 A1 | 12/2008 | Feigenwinter et al. |
| 6,929,606 B2 | 8/2005 | Ritland | | 2009/0124860 A1 | 5/2009 | Miles et al. |
| 6,942,698 B1 | 9/2005 | Jackson | | 2009/0138050 A1 | 5/2009 | Ferree |
| 6,945,933 B2 | 9/2005 | Branch | | 2009/0192403 A1 | 7/2009 | Gharib et al. |
| 6,951,538 B2 | 10/2005 | Ritland | | 2009/0204016 A1 | 8/2009 | Gharib et al. |
| 6,964,687 B1 | 11/2005 | Bernard et al. | | 2010/0069783 A1 | 3/2010 | Miles et al. |
| 6,979,353 B2 | 12/2005 | Bresina | | 2010/0130827 A1 | 5/2010 | Pimenta et al. |
| 6,984,245 B2 | 1/2006 | McGahan et al. | | 2010/0152603 A1 | 6/2010 | Miles et al. |
| 6,986,788 B2 | 1/2006 | Paul et al. | | 2010/0160738 A1 | 6/2010 | Miles et al. |
| 6,989,031 B2 | 1/2006 | Michelson | | 2010/0174148 A1 | 7/2010 | Miles et al. |
| 7,018,416 B2 | 3/2006 | Hanson et al. | | | | |
| 7,033,394 B2 * | 4/2006 | Michelson ............... 623/17.11 | | FOREIGN PATENT DOCUMENTS | | |
| 7,047,082 B1 | 5/2006 | Schrom et al. | | DE | 299 08 259 | 7/1999 |
| 7,050,848 B2 | 5/2006 | Hoey et al. | | EP | 0 369 603 | 5/1990 |
| 7,079,883 B2 | 7/2006 | Marino et al. | | EP | 0 517 030 | 5/1992 |
| 7,089,059 B1 | 8/2006 | Pless | | EP | 0 667 127 | 8/1995 |
| D530,423 S | 10/2006 | Miles et al. | | EP | 0 706 876 | 4/1996 |
| 7,177,677 B2 | 2/2007 | Kaula et al. | | EP | 0 716 840 | 6/1996 |
| 7,198,598 B2 | 4/2007 | Smith et al. | | EP | 0 737 448 | 10/1996 |
| 7,207,949 B2 | 4/2007 | Miles et al. | | EP | 0 796 593 | 9/1997 |
| 7,226,451 B2 | 6/2007 | Shluzas et al. | | EP | 0 880 938 | 2/1998 |
| 7,261,688 B2 | 8/2007 | Smith et al. | | EP | 0 809 974 | 4/1998 |
| 7,470,236 B1 | 12/2008 | Kelleher et al. | | EP | 0 809 975 | 4/1998 |
| 7,473,222 B2 | 1/2009 | Dewey et al. | | EP | 0 811 356 | 4/1998 |
| 7,481,766 B2 | 1/2009 | Lee et al. | | EP | 0 972 538 | 1/2000 |
| 7,522,953 B2 | 4/2009 | Kaula et al. | | FR | 2 795 624 | 1/2001 |
| 7,556,601 B2 | 7/2009 | Branch et al. | | WO | 90/00037 | 1/1990 |
| 7,582,058 B1 | 9/2009 | Miles et al. | | WO | 91/06261 | 5/1992 |
| 7,643,884 B2 | 1/2010 | Pond et al. | | WO | 92/14423 | 9/1992 |
| 7,691,057 B2 | 4/2010 | Miles et al. | | WO | 94/04100 | 3/1994 |
| 7,717,959 B2 | 5/2010 | William et al. | | WO | 94/10928 | 5/1994 |
| 7,819,801 B2 | 10/2010 | Miles et al. | | WO | 95/01810 | 1/1995 |
| 7,935,051 B2 | 5/2011 | Miles et al. | | WO | 96/08205 | 3/1996 |
| 2001/0039949 A1 | 11/2001 | Loubser | | WO | 96/17564 | 3/1996 |
| 2001/0056280 A1 | 12/2001 | Underwood et al. | | WO | 96/41582 | 12/1996 |
| 2002/0007129 A1 | 1/2002 | Marino | | WO | 97/20513 | 6/1997 |
| 2002/0010392 A1 | 1/2002 | Desai | | WO | 97/33525 | 9/1997 |
| 2002/0058950 A1 | 5/2002 | Winterbottom et al. | | WO | 97/37620 | 10/1997 |
| 2002/0072686 A1 | 6/2002 | Hoey et al. | | WO | 98/09586 | 3/1998 |
| 2002/0077632 A1 | 6/2002 | Tsou | | WO | 98/14142 | 4/1998 |
| 2002/0123780 A1 | 9/2002 | Grill et al. | | WO | 98/17208 | 4/1998 |
| 2002/0161415 A1 | 10/2002 | Cohen et al. | | WO | 98/25539 | 6/1998 |
| 2002/0193843 A1 | 12/2002 | Hill et al. | | WO | 99/08627 | 2/1999 |
| 2003/0032966 A1 | 2/2003 | Foley et al. | | WO | 99/38461 | 8/1999 |
| 2003/0105503 A1 | 6/2003 | Marino | | WO | 00/38574 | 7/2000 |

| | | |
|---|---|---|
| WO | 00/45712 | 8/2000 |
| WO | 00/45713 | 8/2000 |
| WO | 00/66217 | 11/2000 |
| WO | 00/67645 | 11/2000 |
| WO | 01/37728 | 5/2001 |
| WO | 01/41681 | 6/2001 |
| WO | 01/49333 | 7/2001 |
| WO | 02/054960 | 7/2002 |
| WO | 03/005887 | 1/2003 |
| WO | 03/026482 | 4/2003 |
| WO | 03/037170 | 5/2003 |
| WO | 2005/013805 | 2/2005 |
| WO | 2005/030318 | 4/2005 |
| WO | 2006/042241 | 4/2006 |
| WO | 2006/066217 | 6/2006 |

OTHER PUBLICATIONS

Dirksmeier et al., "Microendoscopic and Open Laminotomy and Discectomy in Lumbar Disc Disease" Seminars in Spine Surgery, 1999, 11(2): 138-146.
METRx Delivered Order Form, 1999, 13 pages.
Medtronic Sofamor Danek "METRx™ MicroDisectomy System," Medtronic Sofamor Danek USA, 2000, 21 pgs.
Medtronic Sofamor Danek "METRx System Surgical Technique," 2004, 22 pages.
"MetRx System MicroEndoscopic Discectomy: An Evolution in Minimally Invasive Spine Surgery," Sofamor Danek, 1999, 6 pages.
Smith and Foley "MetRx System MicroEndoscopic Discectomy: Surgical Technique" Medtronic Sofamor Danek, 2000, 24 pages.
"Sofamor Danek MED Microendoscopic Discectomy System Brochure" including Rapp "New endoscopic lumbar technique improves access preserves tissue" Reprinted with permission from: Orthopedics Today, 1998, 18(1): 2 pages.
Japanese Patent Office JP Patent Application No. 2006-528306 Office Action with English Translation, Jun. 10, 2009, 4 pages.
Axon 501(k) Notification: Epoch 2000 Neurological Workstation, Dec. 3, 1997, 464 pages.
Foley and Smith, "Microendoscopic Discectomy," Techniques in Neurosurgery, 1997, 3(4):301-307.
Medtronic Sofamor Danek "UNION™ /UNION-L™ Anterior & Lateral Impacted Fusion Devices: Clear choice of stabilization," Medtronic Sofamor Danek, 2000, 4 pages.
NuVasive Vector™ Cannulae, 2000, 1 page.
NuVasive Triad™ Tri-Columnar Spinal EndoArthrodesis™ via Minimally Invasive Guidance, 2000, 1 page (prior to Sep. 25, 2003).
NuVasive Triad™ Cortical Bone Allograft, 2000, 1 page (prior to Sep. 25, 2003).
NuVasive Vertebral Body Access System, 2000, 1 page.
Marina, "New Technology for Guided Navigation with Real Time Nerve Surveillance for Minimally Invasive Spine Discectomy & Arthrodesis," Spineline, 2000, p. 39.
NuVasive "INS-1 Screw Test," 2001, 10 pages.
NuVasive letter re 510k Neuro Vision JJB System, Oct. 16, 2001, 5 pages.
NuVasive letter re 510k Guided Arthroscopy System, Oct. 5, 1999, 6 pages.
NuVasive letter re 510k INS-1 Intraoperative Nerve Surveillance System, Nov. 13, 2000, 7 pages.
"NuVasiveTM Receives Clearance to Market Two Key Elem Minimally Invasive Spine Surgery System," Nov. 27, 2001, 20 pages.
Schick et al., "Microendoscopic lumbar discectomy versus open surgery: an intraoperative EMG study," Eur Spine J, 2002, 11: 20-26.
NuVasive letter re: 510(k) for Neurovision JJB System (Summary), Sep. 25, 2001, 28 pages.
NuVasive letter re: Special 510(k) Premarket Notification: Neurovision JJB System (Device Description), Jul. 3, 2003, 18 pages.
NuVasive letter re: Special 510(k) Premarket Notification: Neurovision JJB System (Device Description), Mar. 1, 2004, 16 pages.
NuVasive letter re: Special 510(k) Premarket Notification: Neurovision JJB System (Device Description), May 26, 2005, 17 pages.
NuVasive letter re: 510(k) Premarket Notification: Neurovision JJB System (Device Description), Jun. 24, 2005, 16 pages.
NuVasive letter re: Special 510(k) Premarket Notification: Neurovision JJB System (Device Description), Sep. 14, 2006, 17 pages.
NuVasive 510(k) Premarket Notification: Neurovision JJB System (Device Description), Aug. 20, 2007, 8 pages.
NuVasive letter re: 510(k) Premarket Notification: Guided Spinal Arthroscopy System (Device Description), Feb. 1, 1999, 40 pages.
NuVasive 510(k) Premarket Notification: Spinal System (Summary), Apr. 12, 2004, 10 pages.
NuVasive 510(k) Summary NIM Monitor, Sep. 4, 1998, 4 pages.
NuVasive correspondence re 510(k) Premarket Notification INS-1 Intraoperative Nerve Surveillance System: Section IV Device Description, pp. 12-51 (prior to Sep. 25, 2003).
Isley et al., "Recent Advances in Intraoperative Neuromonitoring of Spinal Cord Function: Pedicle Screw Stimulation Techniques," American Journal of Electroneurodagnostic Technology, Jun. 1997, 37(2): 93-126.
Mathews et al., "Laparoscopic Discectomy with Anterior Lumbar Interbody Fusion," SPINE, 1995, 20(16): 1797-1802.
Rose et al., "Persistently Electrified Pedicle Stimulation Instruments in Spinal Instrumentation: Techniques and Protocol Development," SPINE, 1997, 22(3): 334-343.
"Electromyography System," International Search report from International Application No. PCT/US00/32329, Apr. 27, 2001, 9 pages.
"Nerve Proximity and Status Detection System and Method," International Search Report from International Application No. PCT/US01/18606, Oct. 18, 2001, 6 pages.
"Relative Nerve Movement and Status Detection System and Method," International Search Report from International Application No. PCT/US01/18579, Jan. 15, 2002, 6 pages.
"System and Method for Determining Nerve Proximity Direction and Pathology During Surgery," International Search Report from International Application No. PCT/US02/22247, Mar. 27, 2003, 4 pages.
"System and Methods for Determining Nerve Direction to a Surgical Instrument," International Search Report from International Application No. PCT/US03/02056, Aug. 12, 2003, 5 pages.
"Systems and Methods for Performing Percutaneous Pedicle Integrity Assessments," International Search Report from International Application No. PCT/US02/35047, Aug. 11, 2003, 5 pages.
"Systems and Methods for Performing Surgery Procedures and Assessments," International Search Report from International Application No. PCT/US02/30617, Jun. 5, 2003, 4 pages.
Lenke et al., "Triggered Electromyographic Threshold for Accuracy of Pedicle Screw Placement," Spine, 1995, 20(4): 1585-1591.
"Brackmann II EMG System," Medical Electronics, 1999, 4 pages.
"Neurovision SE Nerve Locator/Monitor", RLN Systems Inc. Operators Manual, 1999, 22 pages.
"The Brackmann II EMG Monitoring System," Medical Electronics Co. Operator's Manual Version 1.1, 1995, 50 pages.
"The Nicolet Viking IV," Nicolet Biomedical Products, 1999, 6 pages.
Anderson et al., "Pedicle screws with high electrical resistance: a potential source of error with stimulus-evoked EMG," Spine, Department of Orthopaedic Surgery University of Virginia, Jul. 15, 2002, 27(14): 1577-1581.
Bose et al., "Neurophysiologic Monitoring of Spinal Nerve Root Function During Instrumented Posterior Lumber Spine Surgery," Spine, 2002, 27(13):1444-1450.
Calancie et al., "Stimulus-Evoked EMG Monitoring During Transpedicular Lumbosacral Spine Instrumentation" Spine, 1994, 19(24): 2780-2786.
Clements et al., "Evoked and Spontaneous Electromyography to Evaluate Lumbosacral Pedicle Screw Placement," Spine, 1996, 21(5): 600-604.
Danesh-Clough et al. ,"The Use of Evoked EMG in Detecting Misplaced Thoracolumbar Pedicle Screws," Spine, Orthopaedic Department Dunedin Hospital, Jun. 15, 2001, 26(12): 1313-1316.
Darden et al., "A Comparison of Impedance and Electromyogram Measurements in Detecting the Presence of Pedicle Wall Breakthrough," Spine, Charlotte Spine Center North Carolina, Jan. 15, 1998, 23(2): 256-262.

Ebraheim et al., "Anatomic Relations Between the Lumbar Pedicle and the Adjacent Neural Structures," *Spine*, Department of Orthopaedic Surgery Medical College of Ohio, Oct. 15, 1997, 22(20): 2338-2341.

Ford et al. "Electrical Characteristics of Peripheral Nerve Stimulators Implications for Nerve Localization," *Regional Anesthesia*, 1984, 9: 73-77.

Glassman et al., "A Prospective Analysis of Intraoperative Electromyographic Monitoring of Pedicle Screw Placement with Computed Tomographic Scan Confirmation," *Spine*, 1995, 20(12): 1375-1379.

Greenblatt et al., "Needle Nerve Stimulator-Locator: Nerve Blocks with a New Instrument for Locating Nerves," *Anesthesia& Analgesia*, 1962, 41(5): 599-602.

Haig, "Point of view," *Spine*, 2002, 27(24): 2819.

Haig et al., "The Relation Among Spinal Geometry on MRI, Paraspinal Electromyographic Abnormalities, and Age in Persons Referred for Electrodiagnostic Testing of Low Back Symptoms," *Spine*, Department of Physical Medicine and Rehabilitation University of Michigan, Sep. 1, 2002, 27(17): 1918-1925.

Holland et al., "Higher Electrical Stimulus Intensities are Required to Activate Chronically Compressed Nerve Roots: Implications for Intraoperative Electromyographic Pedicle Screw Testing," *Spine*, Department of Neurology, Johns Hopkins University School of Medicine, Jan. 15, 1998, 23(2): 224-227.

Holland, "Intraoperative Electromyography During Thoracolumbar Spinal Surgery," *Spine*, 1998, 23(17): 1915-1922.

Journee et al., "System for Intra-Operative Monitoring of the Cortical Integrity of the Pedicle During Pedicle Screw Placement in Low-Back Surgery: Design and Clinical Results," *Sensory and Neuromuscular Diagnostic Instrumentation and Data Analysis I, 18th Annual International Conference on Engineering in Medicine and Biology Society*, Amsterdam, 1996, pp. 144-145.

Maguire et al., "Evaluation of Intrapedicular Screw Position Using Intraoperative Evoked Electromyography," *Spine*, 1995, 20(9): 1068-1074.

Martin et al. "Initiation of Erection and Semen Release by Rectal Probe Electrostimulation (RPE)," *The Journal of Urology*, The Williams& Wilkins Co., 1983, 129: 637-642.

Minahan et al., "The Effect of Neuromuscular Blockade on Pedicle Screw Stimulation Thresholds," *Spine*, Department of Neurology, Johns Hopkins University School of Medicine, Oct. 1, 2000, 25(19): 2526-2530.

Pither et al., "The Use of Peripheral Nerve Stimulators for Regional Anesthesia: Review of Experimental Characteristics Technique and Clinical Applications," *Regional Anesthesia*, 1985, 10:49-58.

Raj et al., "Infraclavicular Brachial Plexus Block—A New Approach" *Anesthesia and Analgesia*,1973, (52)6: 897-904.

Raj et al., "The Use of Peripheral Nerve Stimulators for Regional Anesthesia," *Clinical Issues in Regional Anesthesia*, 1985, 1(4):1-6.

Raj et al., "Use of the Nerve Stimulator for Peripheral Blocks," *Regional Anesthesia*, Apr.-Jun. 1980, pp. 14-21.

Raymond et al., "The Nerve Seeker: A System for Automated Nerve Localization," *Regional Anesthesia*, 1992, 17(3): 151-162.

Shafik, "Cavernous Nerve Simulation through an Extrapelvic Subpubic Approach: Role in Penile Erection," *Eur. Urol*, 1994, 26: 98-102.

Toleikis et al., "The Usefulness of Electrical Stimulation for Assessing Pedicle Screw Replacements," *Journal of Spinal Disorder*, 2000, 13(4): 283-289.

Medtronic Sofamor Danek "UNION™ /UNION-L™ Anterior & Lateral Impacted Fusion Devices: Surgical Technique" *Medtronic Sofamor Danek*, 2001, 20 pages.

Bergey et al., "Endoscopic Lateral Transpsoas Approach to the Lumbar Spine," *Spine*, 2004, 29(15): 1681-1688.

Dezawa et al., "Retroperitoneal Laparoscopic Lateral Approach to the Lumbar Spine: A New Approach, Technique, and Clinical Trial," *Journal of Spinal Disorders*, 2000, 13(2): 138-143.

Gardocki, "Tubular diskectomy minimizes collateral damage: A logical progression moves spine surgery forward," *AAOS Now*, 2009, 5 pages.

Hovorka et al., "Five years' experience of retroperitoneal lumbar and thoracolumbar surgery," *Eur. Spine J.*, 2000, 9(1): S30-S34.

Kossmann et al., "The use of a retractor system (SynFrame) for open, minimal invasive reconstruction of the anterior column of the thoracic and lumbar spine," *Eur Spine J.*, 2001, 10: 396-402.

Mayer, "A New Microsurgical Technique for Minimally Invasive Anterior Lumbar Interbody Fusion," *Spine*, 1997, 22(6): 691-699.

Mayer, "The ALIF Concept," *Eur Spine J.*, 2000, 9(1): S35-S43.

Mayer and Wiechert, "Microsurgical Anterior Approaches to the Lumbar Spine for Interbody Fusion and Total Disc Replacement," *Neurosurgery*, 2002, 51(2): 159-165.

McAfee et al., "Minimally Invasive Anterior Retroperitoneal Approach to the Lumbar Spine: Emphasis on the Lateral BAK," *Spine*, 1998, 23(13): 1476-1484.

Rao, et al. "Dynamic retraction of the psoas muscle to expose the lumbar spine using the retroperitoneal approach," *J. Neurosurg Spine*, 2006, 5: 468-470.

Wolfla et al., "Retroperitoneal lateral lumbar interbody fusion with titanium threaded fusion cages," *J. Neurosurg (Spine 1)*, 2002, 96: 50-55.

Larson and Maiman, "Surgery of the Lumbar Spine," Thieme Medical Publishers, Inc., 1999, pp. 305-319.

Medtronic XOMED Surgical Products, Inc., NIM-Response Nerve Integrity Monitor Intraoperative EMG Monitor User's Guide, Revision B, 2000, 47 pages.

"NuVasive's spine surgery system cleared in the US," *Pharm & Medical Industry Week*, Dec. 10, 2001, 1 page.

Pimenta, "Initial Clinical Results of Direct Lateral, Minimally Invasive Access to the Lumbar Spine for Disc Nucleus Replacement Using a Novel Neurophysiological Monitoring System." *The 9th IMAST*, May 2002, 1 page.

Pimenta et al., "The Lateral Endoscopic Transpsoas Retroperitoneal Approach (Letra) for Implants in the Lumbar Spine," *World Spine II—Second Interdisciplinary Congress on Spine Care*, Aug. 2003, 2 pages.

Crock, H.V. MD., "Anterior Lumbar Interbody Fusion," Clinical Orthopaedics and Related Research, Number One Hundred Sixty Five, 1982, pp. 157-163, 13 pages.

Mayer and Brock, "Percutaneous endoscopic discectomy: surgical technique and preliminary results compared to microsurgical discectomy," *J. Neurosurg.*, 1993, 78: 216-225.

Schaffer and Kambin, "Percutaneous Posterolateral Lumbar Discectomy and Decompression with a 6.9-Millimeter Cannula," *The Journal of Bone and Joint Surgery*, 1991, 73A(6): 822-831.

Friedman, "Percutaneous discectomy: An alternative to chemonucleolysis," *Neurosurgery*, 1983, 13(5): 542-547.

Brau, "Chapter 22: Anterior Retroperitoneal Muscle-Sparing approach to L2-S1 of the Lumbar Spine," *Surgical Approaches to the Spine*. Robert G. Watkins, MD. (ed) 2003. pp. 165-181.

Kossmann et al., "Minimally Invasive Vertebral Replacement with Cages in Thoracic and Lumbar Spine," *European Journal of Trauma*, 2001, 27: 292-300.

Mayer H. M. (ed.) *Minimally Invasive Spine Surgery: A Surgical Manual*. 2000. 51 pages.

Pimenta et al., "Implante de protese de nucleo pulpost: analise inicial," *Journal Brasileiro de Neurocirurgia*, 2001, 12(2): 93-96.

Traynelis, "Spinal Arthroplasty," *Neurological Focus*, 2002, 13(2): 12 pages.

Zdeblick, Thomas A. (ed.). Anterior Approaches to the Spine. 1999. 43 pages.

CoRoent™ Marketing Brochure (9004001 A.0), *NuVasive, Inc.*, 2004, 2 pages.

CoRoent™ Marketing Brochure (9004001 C.0), *NuVasive, Inc.*, 2005, 2 pages.

CoRoent™ XL & XLR Marketing Brochure (9004225 A.0), *NuVasive, Inc.*, 2005, 2 pages.

CoRoent® XL & XLR Marketing Brochure (9004225 B.0), *NuVasive, Inc.*, 2006, 2 pages.

CoRoent® XL & XLR Marketing Brochure (9004225 C.0), *NuVasive, Inc.*, 2007, 2 pages.

CoRoent® XL Marketing Brochure (9500039 A.0), *NuVasive, Inc.*, 2006, 8 pages.

Baulot et al., "Complementary anterior spondylodesis by thoracoscopy. Technical note regarding an observation," *Lyon Surg.*, 1994, 90(5):347-351.

Berry et al., "A morphometric study of human lumbar and selected thoracic vertebrae, study of selected vertebrae," *Spine*, 1996, 12(4):362-367.

Crock, H. V., "A Short Practice of Spinal Surgery," Second, revised edition, published by Springer-Verlag/Wein, New York (1993).

Edeland, H.G., "Some additional suggestions for an intervertebral disc prosthesis," *Journal of Biomedical Engineering*, 1985, 7:57-62.

Kemp, H. B. S., "Anterior fusion of the spine for infective lesions in adults," *Journal of Bone & Joint Surgery*, 1973, 55B(4):715-734.

Alleyne et al., "Current and future approaches to lumbar disc surgery: A literature review", *Medscape Orthopedics & Sports Medicine*, [www.medscape.com/Medscape/OrthoSportsMed/1997/v01.n11/.../mos3057], 1997, 14 pages.

Benini et al., "Undercutting decompression and posterior fusion with translaminar facet screw fixation in degenerative lumbar spinal stenosis: Technique and results," *Neuro-Orthopedics*, 1995, 17/18: 159-172.

Kambin and Zhou, "History and current status of percutaneous arthroscopic disc surgery," *Spine*, 1996, 21(24S):57S-61S.

Stein et al., "Percutaneous facet joint fusion: Preliminary experience," *Journal of Vascular and Interventional Radiology*, 1993, 4:69-74.

Vamvanu et al., "Surgical treatment of internal disc disruption: An outcome study of four fusion techniques," *Journal of Spinal Disorders*, 1998, 11(5):375-382.

\* cited by examiner

METHOD AND APPARATUS FOR PERFORMING SPINE SURGERY

CROSS-REFERENCE TO RELATED APPLICATIONS

This application is an non-provisional patent application and claiming the benefit of priority from commonly owned and U.S. Provisional Patent Application Ser. No. 61/212,921, entitled "Method and Apparatus for Performing Spine Surgery," filed on Apr. 16, 2009, and U.S. Provisional Patent Application Ser. No. 61/319,823, entitled "Ligament Resector and Related Methods," filed on Mar. 31, 2010, the entire contents of which is hereby expressly incorporated by reference into this disclosure as if set forth in its entirety herein.

FIELD

The present invention relates to implants and methods for adjusting sagittal imbalance of a spine.

BACKGROUND

A human spine has three main regions—the cervical, thoracic, and lumbar regions. In a normal spine, the cervical and lumbar regions have a lordotic (backward) curvature, while the thoracic region has a kyphotic (forward) curvature. Such a disposition of the curvatures gives a normal spine an S-shape. Sagittal imbalance is a condition in which the normal alignment of the spine is disrupted in the sagittal plane causing a deformation of the spinal curvature. One example of such a deformity is "flat-back" syndrome, wherein the lumbar region of the spine is generally linear rather than curved. A more extreme example has the lumbar region of the spine exhibiting a kyphotic curvature such that the spine has an overall C-shape, rather than an S-shape. Sagittal imbalance can be a problem in that it is biomechanically disadvantageous and generally results in discomfort, pain, and an awkward appearance in that the patient tends to be bent forward excessively.

Various treatments for sagittal imbalance are known in the art. These treatments generally involve removing at least some bone from a vertebra (osteotomy) and sometimes removal of the entire vertebra (vertebrectomy), in order to reduce the posterior height of the spine in the affected region and recreate lordotic curve. Such procedures are traditionally performed via an open, posterior approach involving a large incision (often to expose multiple spinal levels at the same time) and require stripping of the muscle tissue away from the bone. These procedures can have the disadvantages of a large amount of blood loss, high risk, and a long and painful recovery for the patient. Furthermore, depending upon the patient, multiple procedures, involving both anterior and posterior approaches to the spine, may be required.

The present invention is directed at overcoming, or at least improving upon, the disadvantages of the prior art.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DESCRIPTION OF A PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The methods and devices described herein include a variety of inventive features and components that warrant patent protection, both individually and in combination.

Figure 1:
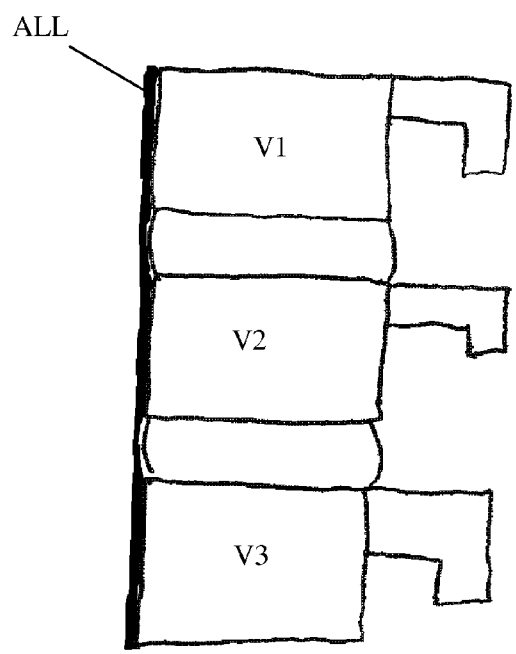
FIG. 1 is a lateral view representing a portion of a sagitally imbalanced lumbar spine lacking the normal lordotic curvature.
Figure 2:
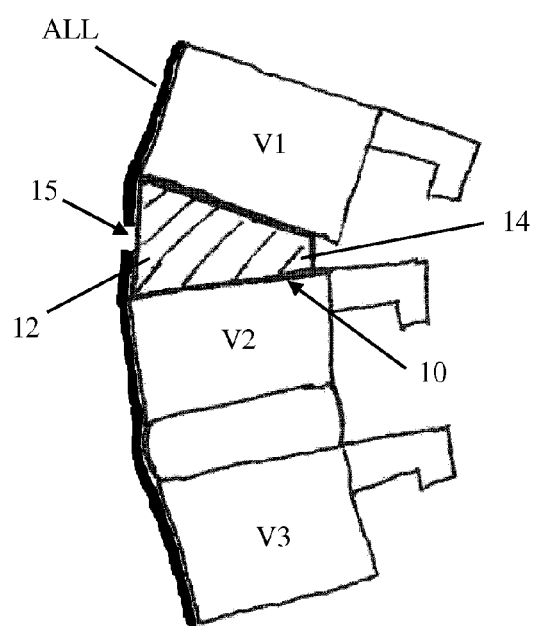
FIG. 2 is a side view representing the lumbar spine of FIG. 1 after restoration of the lordotic curvature using a hyper-lordotic fusion implant, according to one example embodiment.

With reference to FIGS. 1-2, devices and methods of the present invention are utilized to correct sagittal imbalance, including lumbar kyphosis, by increasing the anterior height of the affected spinal area (as opposed to reducing the posterior height). FIG. 1 illustrates a portion of the lumbar spine lacking the standard lordotic curvature. To correct the sagittal imbalance, illustrated in FIG. 2, a hyper-lordotic implant 10 is positioned into the disc space at the appropriate spinal level (e.g. between V1 and V2). An anterior sidewall 12 of hyper-lordotic implant 10 has a height significantly larger than an opposing posterior sidewall 14 such that when the implant is positioned within the disc space the anterior aspects of V1 and V2 are forced apart while the posterior aspects are not (or at least not to the same degree), thus imparting a lordotic curvature into the spine. To allow the anterior aspects of V1 and V2 to separate and receive the hyper-lordotic implant 10, the Anterior Longitudinal Ligament (ALL) that runs along the anterior aspect of the spine may be released or cut (15). According to a preferred method, the implant 10 is implanted through a lateral access corridor formed through the side of the patient. Accessing the targeted spinal site through the lateral access corridor avoids a number of disadvantages associated with posterior access (e.g. cutting through back musculature and possible need to reduce or cut away part of the posterior bony structures like lamina, facets, and spinous process) and anterior access (e.g. use of an access surgeon to move various organs and blood vessels out of the way in order to reach the target site). Accordingly, by accessing the target site via a lateral access approach and correcting the sagittal imbalance without reducing the posterior height (i.e. no bone removal) the high blood loss and painful recovery associated previous methods may be avoided (or at least mitigated).

Figure 3:
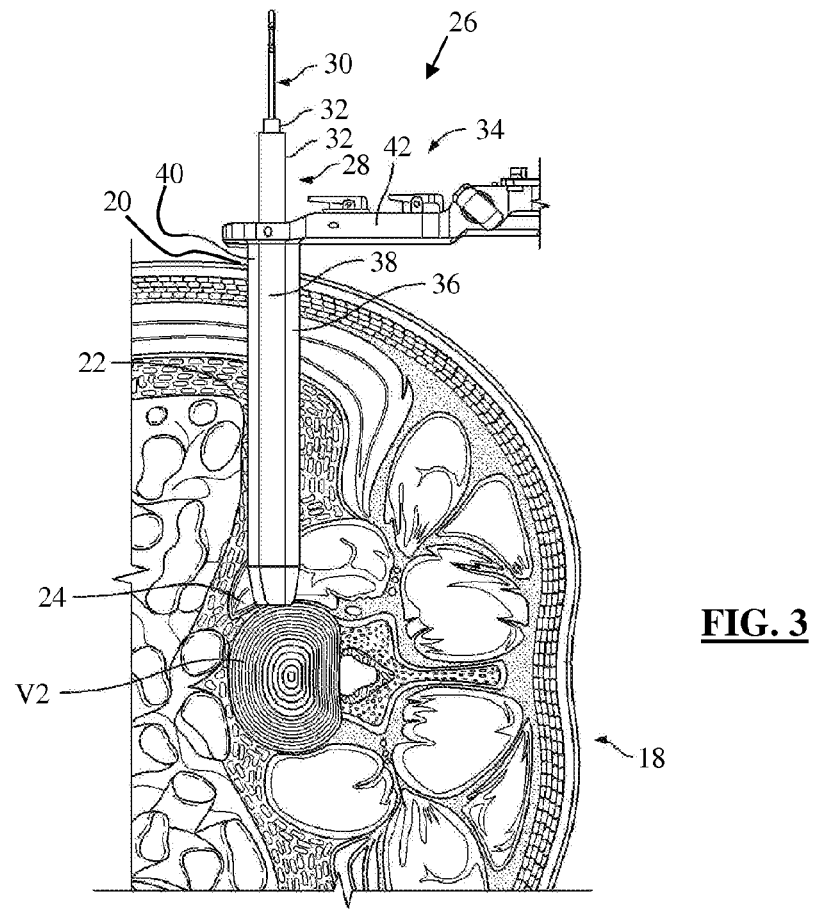
FIG. 3 is a top down view depicting the creation of a lateral access corridor formed with surgical access system through the side of the patient to the target disc space, according to one example embodiment.
Figure 4:
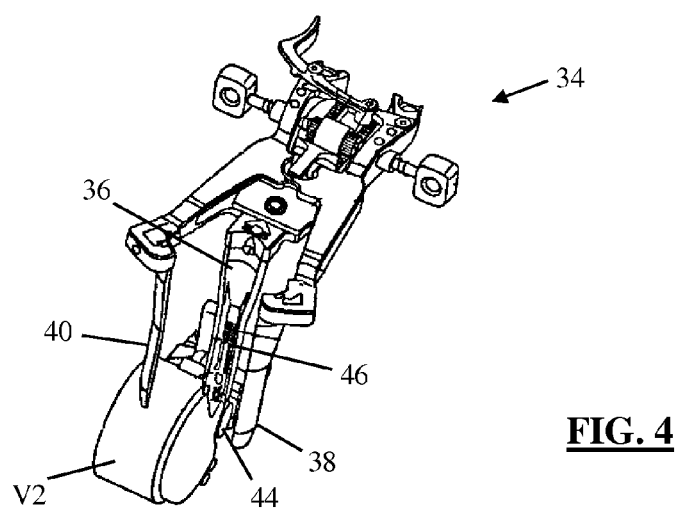
FIG. 4 is a perspective view depicting a lateral access corridor formed with a retractor assembly through the side of the patient to the target disc space, according to one example embodiment.
Figure 5:
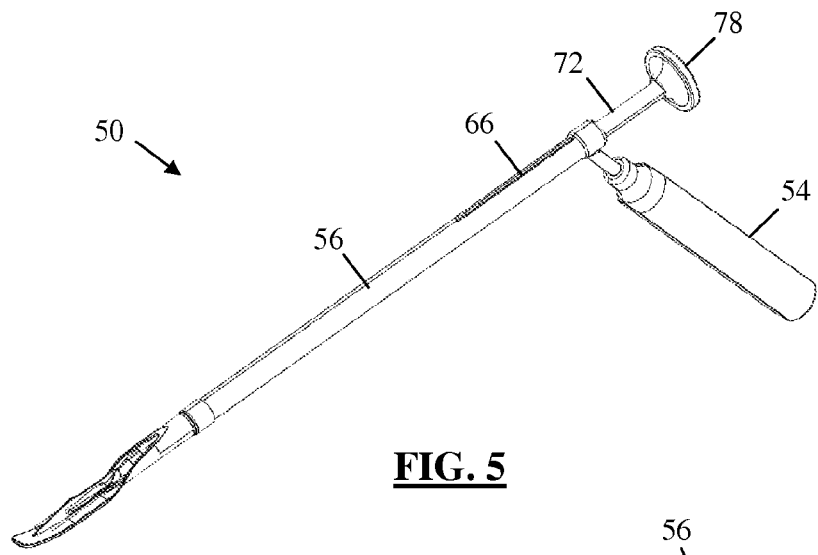
FIG. 5 is a front perspective view of an Anterior Longitudinal Ligament (ALL) resector for safely releasing the ALL through a lateral access corridor, according to one example embodiment.
Figure 6:
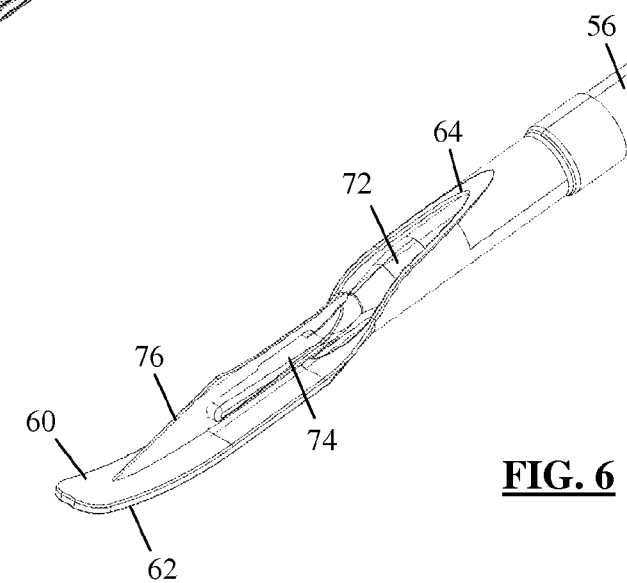
FIG. 6 is an enlarged from perspective view of the distal portion of the ALL resector of FIG. 5.
Figure 7:
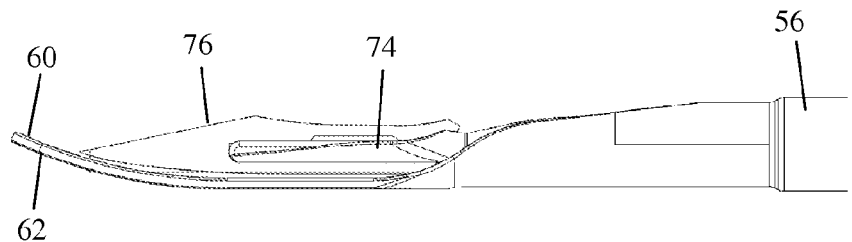
FIG. 7 is an enlarged side view of the distal portion of the ALL resector of FIG. 5.

According to one example, the lateral access approach to the targeted spinal space may be performed according to the instruments and methods described in commonly owned U.S. Pat. No. 7,207,949 entitled "Surgical Access System and Related Methods," and/or U.S. patent application Ser. No. 10/967,668 entitled "Surgical Access System and Related Methods," the entire contents of which are each incorporated herein by reference as if set forth herein in their entireties. With reference to FIGS. 3-4, a discussion of the lateral access instruments and methods is provided in brief detail. With the patient 20 positioned on their side, a surgical access system 20 is advanced through an incision 20, into the retroperitoneal space 22, and then through the psoas muscle 24 until the targeted spinal site (e.g. the disc space between V1 and V2) is reached. The access system 26 may include at least one tissue dilator, and preferably includes a sequential dilation system 28 with an initial dilator 30 and one or more additional dilators 32 of increasing diameter, and a tissue retractor assembly 34. As will be appreciated, the initial dilator 30 is preferably advanced to the target site first, and then each of the additional dilators 32 of increasing diameter are advanced in turn over the previous dilator. A k-wire (not shown) may be advanced to the target site and docked in place (for example, by inserting the k-wire into the vertebral disc) prior to, in concurrence with, or after advancing the initial dilator 30 to the target site. With the sequential dilation system 28 positioned adjacent the target site (and optionally docked in place via the k-wire), the retractor assembly 34 is then advanced to the target site over the sequential dilation system 28. According to the embodiment shown, the retractor assembly 34 includes retractor blades 36, 38, 40 and a body 42. With the sequential dilation system 28 removed, the retractor blades 36, 38, and 40 are separated (FIG. 5), providing the lateral access corridor through which instruments may be advanced to prepare the disc space and insert the implant 10. According to one example, the posterior blade 36 may be fixed in position relative to the spine prior to opening the retractor blades. This may be accomplished, for example by attaching a shim to the blade 36 (e.g. via track 44 including dove tail grooves formed on the interior of blade 36) and inserting the distal end of the shim into the disc space. In this manner, the posterior blade 36 will not move posteriorly (towards nerve tissue located in the posterior portion of the psoas muscle). Instead, the blades 38 and 40 will move away from the posterior blade 36 to expand the access corridor. Additionally, nerve monitoring (including determining nerve proximity and optionally directionality) is preferably performed as each component of the access system 26 is advanced through the psoas muscle, protecting the delicate nerve tissue running through the psoas, as described in the '949 patent and '668 application. Monitoring the proximity of nerves also allows the posterior blade 36 of the retractor assembly 34 to be positioned very posterior (all the way back to the exiting nerve roots), thus exposing a greater portion of the disc space than would otherwise be safely achievable. This inturn permits full removal of the disc and implantation of a wider implant and the wider implant makes utilization of the hyper-lordotic implant with a large lordotic angle (e.g. between 20-40 degrees) more practical.

With the lateral access corridor formed (as pictured in FIG. 5) the target site may be prepped for insertion of the implant 10. Preparation of the disc space may include performing an annulotomy, removal of disc material, and abrasion of the endplates and instruments such as annulotomy knives, pituitaries, curettes, disc cutters, endplate scrapers may be used. Additionally, as discussed above, it may generally be necessary to release the ALL in order to create enough flexibility between the adjacent vertebrae (e.g. V1 and V2) to receive the hyper-lordotic implant 10. Unlike an anterior approach (where the great vessels and other tissue lying anterior to the disc space is retracted during the approach), when the target disc is approached laterally, the great vessels remain adjacent to the ALL along the anterior face of the spine. Thus, while cutting the ALL is generally simple and necessary during an anterior approach surgery, cutting the ALL during a lateral approach surgery has typically been unnecessary and can be difficult because of the need to avoid damaging the great vessels. Accordingly, FIGS. 5-14 set forth various example embodiments of ALL resecting instruments for safely releasing the ALL from a lateral approach.

FIGS. 5-8 illustrate one example ALL resector 50. The ALL resector 50 includes a tissue retractor 52 and a sliding blade 68 and functions to both sever the ALL and protect surrounding tissue (e.g. great vessels, nerves etc. . . . ) from unwanted damage while the ALL is being severed. The tissue retractor 52 includes a handle 54, hollow shaft 56, and head 58. The head 58 is curved, preferably such that the inside surface 60 complements the curvature of the anterior aspects of the spinal target site. The head 58 may thus be positioned through the lateral access corridor to the spine and such that the curved interior surface 60 nestles around the anterior curved anterior aspect of the spine. The outside surface 62 will form a barrier, protecting tissue along the anterior spine from inadvertent contact with the sliding blade when the ALL is cut. Furthermore, the tissue retractor 52 can be further manipulated move tissue and further expose the anterior aspect of the target site. The hollow shaft 56 includes a central lumen 64 with an opening adjacent the head 58 and another opening at the opposing end such that the sliding blade 54 may travel through the shaft 56.

The sliding blade 68 includes a blade 70 that is secured to the distal end of an extender 72 by way of an attachment feature 74. The attachment feature 74 as shown is similar to known attachment features used for attaching a blade at the end of a scalpel. It will be appreciated that any number of mechanisms may be used to attach blade 70 to extender 72. Blade 70 may be disposable and extender 72 may be reusable. Alternatively, both blade 70 and extender 72 may be reusable or both may be disposable. The blade 70 includes a cutting edge 76 that, when advanced beyond the lumen 64 of shaft 56, cuts through tissue or material situated adjacent the cutting edge 76.

The proximal end of the extender 72 includes a grip 78 that a user may use to manipulate the position of the sliding blade 40 relative to the shaft 56 and head 58. At least one stop feature 80 extends from the outer surface of the extender 72 which engages with a track 66 that extends along a portion of the elongated shaft 56. The track 66 limits the longitudinal travel of the sliding blade 68 relative to the shaft 56 so that the sliding blade 68 remains slidably mated to the tissue retractor 52 without becoming unassembled and such that the blade 70 cannot extend beyond the protective head 58. Additionally, the stop feature 80 restricts rotation of the sliding blade 68 relative to the tissue retractor 52.

Figure 8:
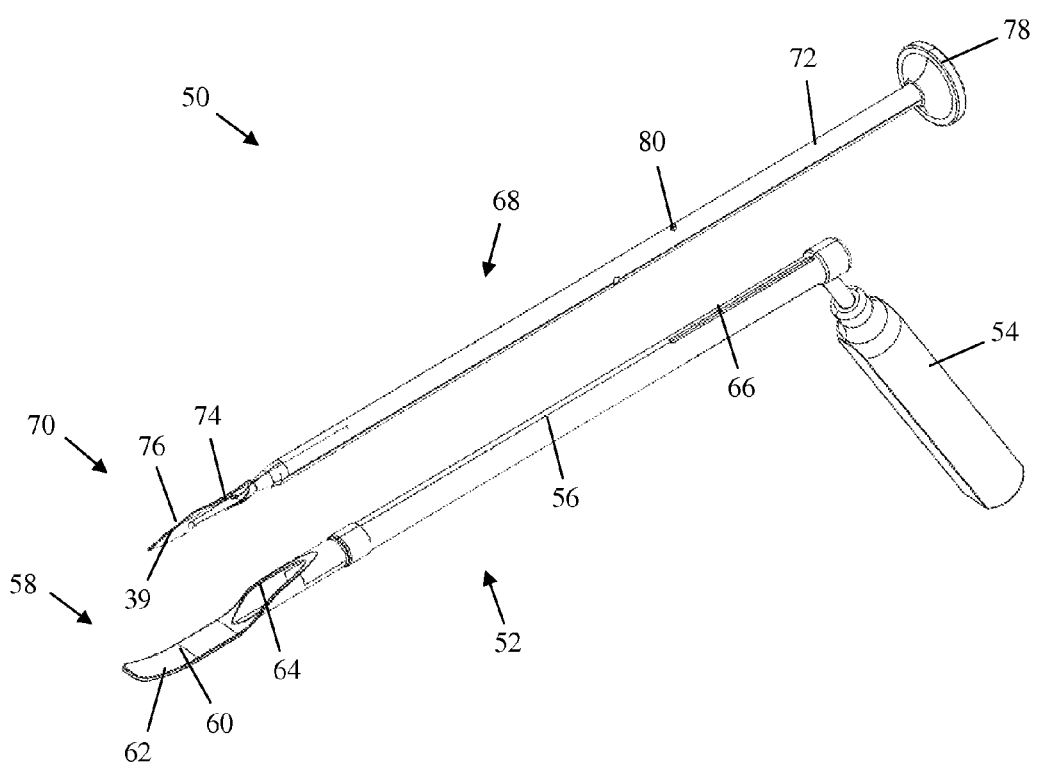
FIG. 8 is an exploded front perspective view of the ALL resector of FIG. 5.
Figure 9:
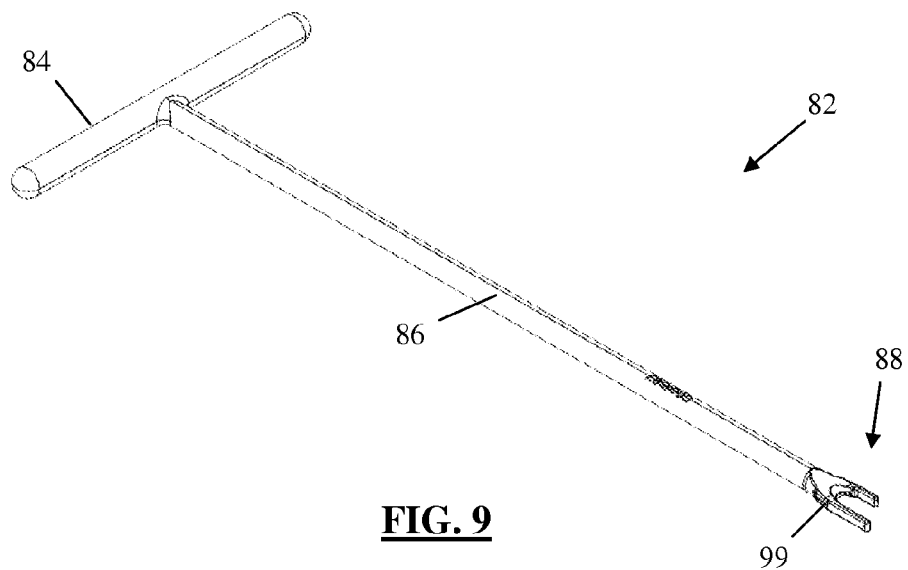
FIG. 9 is a front perspective view of an ALL resector for safely releasing the ALL through a lateral access corridor, according to another example embodiment.
Figure 10:
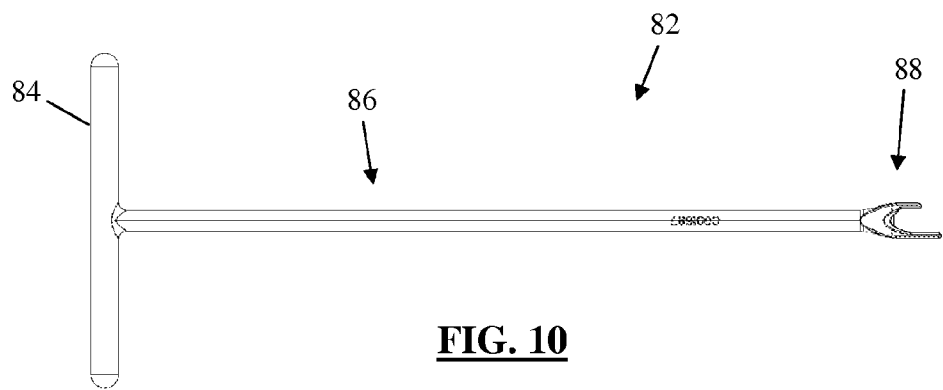
FIG. 10 is a side view of the ALL resector of FIG. 9.
Figure 11:
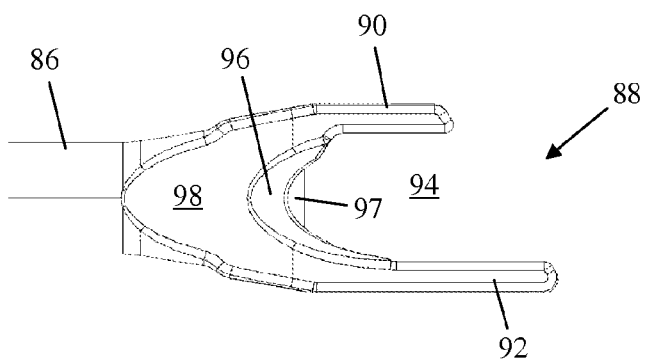
FIG. 11 is an enlarged side view of the distal end of the ALL resector of FIG. 9.
Figure 12:
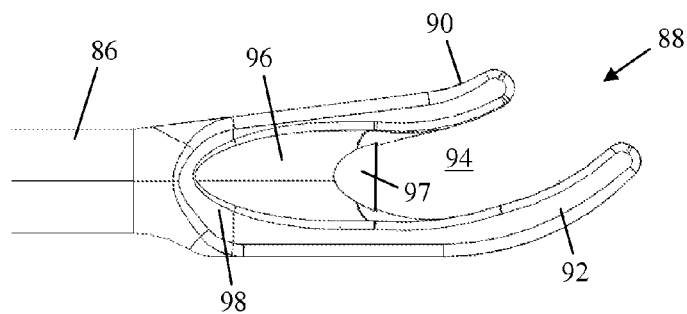
FIG. 12 is an enlarged side view of the distal end of the ALL resector of FIG. 9 having curved finger portions.

FIGS. 9-8 illustrate another example embodiment of an ALL resector 82. The ALL resector 82 includes a handle 84 (for example, a T-handle) located at the proximal end of the elongated shaft 86 and a distal head 88 for resecting the ALL. The distal head 88 includes distally extending first and second fingers 90, 92, which form an opening 94 therebetween. First and second tapered surfaces 96, 98 which extend a distance from the elongated shaft 84 along the fingers 90, 92 enable the distal head 88 to insert gently between tissue. As best shown in FIG. 11, the first finger 90 may be shorter in length than the second finger 92. However, the first and second finger 90, 92 may be provided in any number of length configurations without departing from the scope of the present invention. By way of example, it has been contemplated that the first finger 14 may be completely removed. Alternatively, as pictured in FIG. 12, the fingers 90 and 92 may be curved and have a more substantial width than shown in FIGS. 9-11. The curvature of the first and second fingers allows the distal head 88 to follow closely along the anterior side of the spine and/or along a curved spatula (not shown) positioned adjacent the anterior side of the vertebral body. Though not shown, a user may optionally insert a spatula along the anterior portion of the ALL prior to inserting the ALL retractor 82. The spatula may serve as additional protection between the delicate tissue anterior to the ALL and the cutting blade 97 of the ALL resector 82. With a spatula in place the user may insert the distal head 88 such that it approaches the lateral side of the ALL and is guided along the inside edge of the spatula. By way of example, the spatula may be straight or curved to match the selected fingers of the distal head 88.

A cutting blade 97 is exposed between the first and second fingers 90, 92 in the opening 17. A slot 99 formed along a side of the distal head 88 allows a cutting blade 97 to be inserted and removed from the distal head 88. Thus, the cutting blade 97 may be disposable and the remainder of the ALL resector 82 may be reusable. Alternatively, both cutting blade 97 and remainder of the ALL resector 82 may be reusable or both may be disposable. In use, the ALL resector 82 is preferably positioned such that the second finger 92 is aligned along the anterior side of the ALL and the first finger 90 is aligned along the posterior side of the ALL, thus, at least partially bounding the ALL on either side. The ALL resector 82 is advanced forward so that the cutting blade 97 cuts through the ALL from one lateral edge to the other. As discussed above, the second finger 92 is preferably aligned along the anterior side of the ALL as the distal head 88 is advanced, thereby shielding the tissue lying anterior to the finger 92 (e.g. great vessels, etc. . . . ) from the cutting blade 97. Furthermore, as the user advances the ALL resector 82, the fingers 90, 92 may also act as a stabilizing guide.

Figure 13:
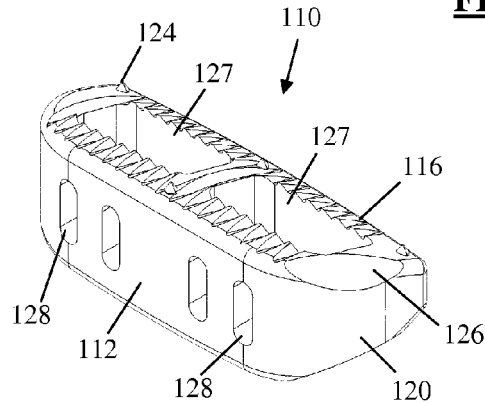
FIGS. 13-15 are anterior-front perspective, posterior-rear perspective, and front views of a hyper-lordotic lateral implant according to one example embodiment.
Figure 14:
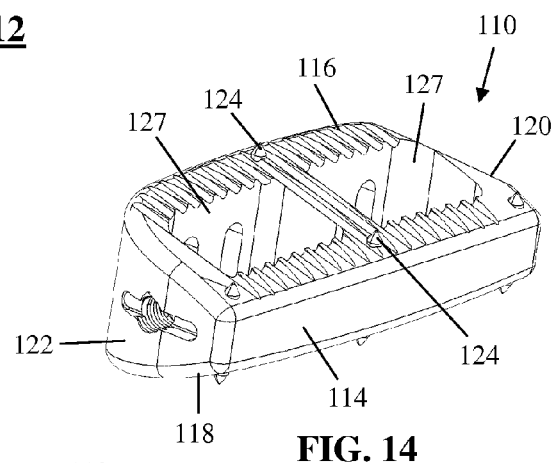
Figure 15:
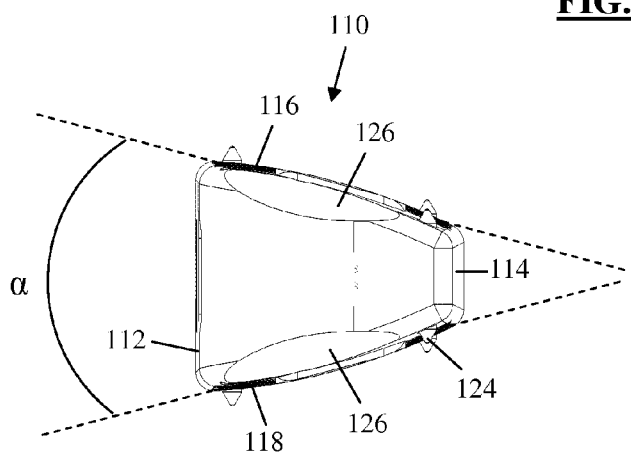

Turning now to FIGS. 13-19, various embodiments of the hyper-lordotic implant 10 are described. FIGS. 13-15, for example, illustrate an example implant 110. Implant 110 may preferably be comprised of any suitable non-bone composition having suitable radiolucent characteristics, including but not limited to polymer compositions (e.g. poly-ether-ether-ketone (PEEK) and/or poly-ether-ketone-ketone (PEKK)) or any combination of PEEK and PEKK. Other materials such as for example, metal, ceramics, and bone may also be utilized for the implant 110. Implant 110 has a top surface 116 and bottom surface 118 for contacting V1 and V2, anterior sidewall 112, posterior sidewall 114, and front or leading side 120, and rear or trailing side 122. As discussed, the anterior sidewall 112 has a height greater than the posterior sidewall 114 such that the top surface 116 and bottom surface 118 converge towards each other in the posterior direction. By way of example, the top and bottom surfaces may converge at an angle between 20 and 40 degrees. It is contemplated that variations of the implant 110 may be simultaneously provided such that the user may select from different available ranges. For example, variations may be provided with 20 degree, 30 degree, and 40 degree angles. The top and bottom surfaces may be planar or provided as convex to better match the natural contours of the vertebral end plates. The length of the implant 110 is such that it may span from one lateral aspect of the disc space to the other, engaging the apophyseal ring on each side. By way of example, the implant 110 may be provided with a length between 40 mm and 60.

Having been deposited in the disc space, the implant 110 facilitates spinal fusion over time by maintaining the restored curvature as natural bone growth occurs through and/or past the implant 10, resulting in the formation of a boney bridge extending between the adjacent vertebral bodies.

The implant 110 may be provided with any number of additional features for promoting fusion, such as apertures 127 extending between the top and bottom surfaces 116-117 which allow a boney bridge to form through the implant 110. Various osteoinductive materials may be deposited within the apertures 127 and/or adjacent to the implant 110 to further facilitate fusion. Such osteoinductive materials may be introduced before, during, or after the insertion of the exemplary spinal fusion implant 110, and may include (but are not necessarily limited to) autologous bone harvested from the patient receiving the spinal fusion implant, bone allograft, bone xenograft, any number of non-bone implants (e.g. ceramic, metallic, polymer), bone morphogenic protein, and bio-resorbable compositions, including but not limited to any of a variety of poly (D,L-lactide-co-glycolide) based polymers. Visualization apertures 128 situated along the sidewalls, may aid in visualization at the time of implantation and at subsequent clinical evaluations. More specifically, based on the generally radiolucent nature of the preferred embodiment of implant 110, the visualization apertures 128 provide the ability to visualize the interior of the implant 110 during X-ray and/or other suitable imaging techniques. Further, the visualization apertures 128 will provide an avenue for cellular migration to the exterior of the implant 110. Thus the implant 110 will serve as additional scaffolding for bone fusion on the exterior of the implant 110.

The implant 110 also preferably includes anti-migration features designed to increase the friction between the implant 110 and the adjacent contacting surfaces of the vertebral bodies V1 and V2 so as to prohibit migration of the implant 110 after implantation. Such anti-migration features may include ridges provided along the top surface 116 and/or bottom surface 118. Additional anti-migration features may also include spike elements 124 disposed along the top and bottom surfaces.

Tapered surfaces 126 may be provide along the leading end 120 to help facilitate insertion of the implant 110. Additional instrumentation may also be used to help deploy the implant 110 into the disc space. By way of example, the implant installation device shown and described in detail in the commonly owned and copending U.S. patent application Ser. No. 12/378,685, entitled "Implant Installation Assembly and Related Methods," filed on Feb. 17, 2009, the entire contents of which is incorporated by reference herein, may be used to help distract the disc space and deposit the implant therein.

Figure 16:
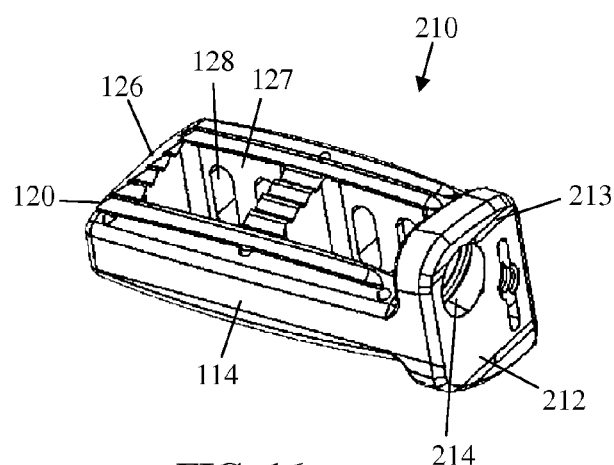
FIGS. 16-17 are posterior-rear perspective and rear views of a hyper-lordotic lateral implant according to another example embodiment.
Figure 17:
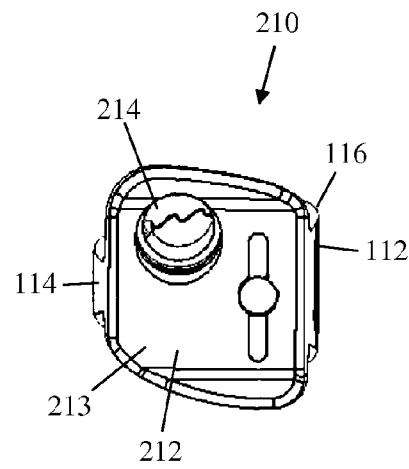

FIGS. 16-17 illustrate an implant 210 according to another example embodiment. The implant 210 share many similar features with the implant 110 such that like feature are numbered alike and repeat discussion in not necessary. The implant 210 differs from the implant 110 in that a trailing side 212 is configured for fixed engagement to one of the adjacent vertebral bodies (i.e. V1 or V2) to supplement the anti migration features and ensure the hyper-lordotic implant is not projected out of the disc space. Specifically, the implant 210 includes a tab 213 extending vertically above the top surface 116 and/or below the bottom surface 118. Tabs 213 facilitate fixation of the implant 210 to the adjacent vertebrae. In the example shown in FIGS. 16-17, the tab 213 extends past both the bottom and top surfaces 118 and 116, respectively. It will be appreciated, however, that the implant 210 may include, without departing from the scope of the present invention and by way of example only, a tab 213 that extend solely in one direction. Additionally, multiple tabs 210 of various sizes and/or shapes may be used throughout a single implant 210 to facilitate implantation or fixation. In the illustrated example, the tab has a single fixation aperture 214 for enabling the engagement of a fixation anchor (not shown) within the vertebral bone to secure the placement of the implant. In use, when the implant 210 is positioned within the disc space, the tab 213 engages the exterior of the upper and lower vertebra and the fixation anchor may be driven into the side of either the upper or lower vertebra. One will appreciate that various locking mechanism may be utilized and positioned over or within the fixation aperture 214 to prevent the fixation anchor from unwanted disengagement with the implant 210. For example, a suitable locking mechanism may be in the form of a canted coil disposed within the fixation aperture 214 or a screw that may be engaged to the trailing end 212 and cover all or a portion of the fixation aperture 214 after the fixation anchor positioned.

Figure 18:
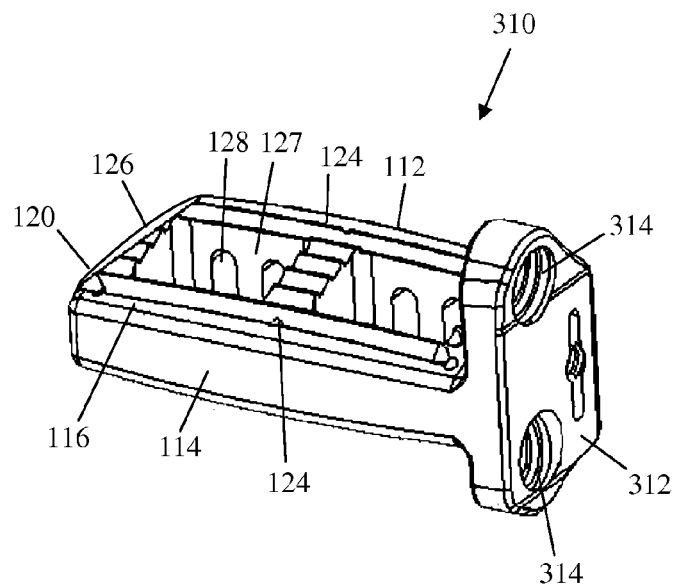
FIGS. 18-19 are posterior-rear perspective and rear views of a hyper-lordotic lateral implant according to still another example embodiment.
Figure 19:
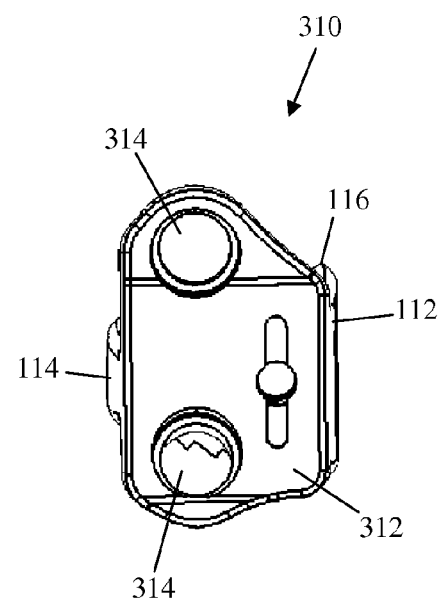

FIGS. 18-19 illustrate an implant 310 according to another example embodiment. The implant 310 shares many similar features with the implants 110 and 110 such that like feature are numbered alike and repeat discussion in not necessary. The implant 310 differs from the implant 110 in that a trailing side 312 is configured for fixed engagement to one of the adjacent vertebral bodies (i.e. V1 or V2) to supplement the anti migration features and ensure the hyper-lordotic implant is not projected out of the disc space. Specifically, the implant 310 includes a tab 313 extending vertically above the top surface 116 and/or below the bottom surface 118. Tab 313 facilitates fixation of the implant 310 to the adjacent vertebrae. Tab 313 extends past both the bottom and top surfaces 118 and 116, respectively. It will be appreciated, however, multiple tabs 310 of various sizes and/or shapes may be used throughout a single implant 310 to facilitate implantation or fixation. The implant 310 differs from the implant 210 in that the tab 213 has includes a pair of fixation apertures 214 for enabling the engagement of a pair fixation anchors (not shown) within the vertebral bone to secure the placement of the implant. In use, when the implant 310 is positioned within the disc space, the tab 313 engages the exterior of the upper and lower vertebra and a fixation anchor is driven into the side of each of the upper or lower vertebra. One will appreciate that various locking mechanism may be utilized and positioned over or within the fixation apertures 314 to prevent the fixation anchors from unwanted disengagement with the implant 310. One will also appreciate that single locking mechanism may be used to cover both fixation apertures 314, or, a separate locking mechanism may be used to cover each fixation aperture 314. Again, by way of example, a suitable locking mechanism may be in the form of a canted coil disposed within each fixation aperture 314 or a screw that may be engaged to the trailing end 312 and cover all or a portion of each fixation aperture 314 after the fixation anchors are positioned.

While this invention has been described in terms of a best mode for achieving this invention's objectives, it will be appreciated by those skilled in the art that variations may be accomplished in view of these teachings without deviating from the spirit or scope of the invention. For example, particularly at L5-S1 where the pelvic bone makes a lateral access approach difficult, an antero-lateral approach similar to the approach utilized during appendectomies may be utilized.

What is claimed is:

1. A method for correcting saggital imbalance of a lumbar spine, comprising the steps of:
    inserting an access system along a lateral, trans-psoas path to a target site on the lumbar spine to create an operative corridor to the target site, wherein the access system comprises a stimulation electrode and is inserted under conditions wherein an electrical stimulation signal is delivered through said stimulation electrode for nerve monitoring when the stimulation electrode is positioned in the lateral, trans-psoas path;
    preparing the intervertebral space between first and second vertebra of the lumbar spine for receipt of an intervertebral implant, the intervertebral space being at least partially defined by an anterior aspect, a posterior aspect, and opposing first and second lateral aspects;
    inserting a cutting device through the operative corridor along the lateral, trans-psoas path and severing the Anterior Longitudinal Ligament (ALL); and
    advancing the intervertebral implant through the operative corridor along the lateral, trans-psoas path into the intervertebral disc space between the first and second vertebra, the intervertebral implant having an upper surface to contact said first vertebra when the implant is positioned in the intervertebral space, a lower surface to contact the second vertebra when the implant is positioned in the intervertebral space, a first lateral wall and second lateral wall defining a longitudinal length therebetween, the longitudinal length being such that the implant extends from the apophyseal ring at the first lateral aspect to the apophyseal ring at the second lateral aspect when the implant is positioned in the intervertebral disc space, an anterior sidewall to face the anterior aspect of the intervertebral disc space when the implant is positioned in the intervertebral disc space, and a posterior sidewall to face the posterior aspect of the intervertebral disc space when the implant is positioned in the intervertebral disc space, the anterior sidewall and posterior sidewall defining a width therebetween, the anterior sidewall having a first height and the posterior sidewall having a second height smaller than the first height such that the upper and lower surfaces increase in slope from the posterior sidewall to the anterior sidewall forming an angle ranging from 20 degrees to 40 degrees.

2. The method of claim 1, comprising the additional step of anchoring the implant to at least one of said adjacent vertebra the first vertebra and the second vertebra.

3. The method of claim 2, wherein the second lateral sidewall includes an extension tab that abuts a lateral aspect of at least one of the first vertebra and second vertebra when the implant is positioned in the intervertebral space, the extension tab including at least one aperture that receives a fixation anchor therethrough, wherein the step of anchoring the implant comprises advancing an anchor through the at least one aperture into one of the first and second vertebra.

4. The method of claim 3, wherein the extension tab includes an upper portion including a first aperture that abuts a lateral aspect of first vertebra and a lower portion including a second aperture that abuts a lateral aspect of the second, and wherein the step of anchoring the implant comprises advancing an anchor through the first aperture into the first vertebra and advancing a second anchor through the second aperture into second vertebra.

5. The method of claim 1, wherein longitudinal length is between 40 mm and 60 mm.

6. The method of claim 1, wherein the upper surface and lower surface are planar surfaces.

7. The method of claim 6, wherein the upper surface and lower surfaces are convex surfaces.

8. The method of claim 1, wherein the implant is a fusion implant and includes at least one fusion aperture opening in the upper surface and lower surface to permit bone growth between the first vertebra and second vertebra.

9. The method of claim 8, comprising the additional step of depositing bone growth promoting substances within the at least one fusion aperture before, during, and/or, after advancing the implant into the intervertebral disc space.

10. The method of claim 1, wherein the top surface includes anti-migration features that contact the first vertebra and the bottom surface includes anti-migration features that contact the lower vertebra.

11. The method of claim 1, wherein the step of severing the ALL comprises protecting the great vessels while the ALL is being severed.

12. The method of claim 11, wherein protecting the great vessels comprising positioning a barrier between the Great Vessels and a cutting element of the cutting device.

13. The method of claim 12, wherein the barrier is part of the cutting device.

14. The method of claim 13, wherein the cutting device includes a distal head with an outer finger, and inner finger, and a cutting blade exposed between the outer finger and inner finger, each of the outer finger and inner finger extending beyond the cutting blade, the outer finger extending beyond the inner finger, wherein the step of severing the ALL comprises advancing the outer finger along the outer surface of the ALL until the cutting blade cuts completely through the ALL.

15. The method of claim 14, wherein at least the outer finger is curved.

16. The method claim 13, wherein the cutting device includes a tissue retractor and a sliding blade, the tissue retractor having a head with curvature that generally complements the curvature of the anterior aspect of the lumbar spine and the step of severing the ALL comprises positioning the tissue retractor such that the head nestles around the ALL forming the barrier and sliding the sliding blade distally along the inner surface of the retractor head.

17. The method of claim 1, wherein the access system comprises at least one dilator having a stimulation electrode situated on a distal end and a retractor that slides over the at least one dilator in a first configuration, and there after adjusts to a second configuration to enlarge the create the enlarge the operative corridor.

18. The method claim 17, wherein the nerve monitoring includes determining a proximity and direction to a nerve located in the psoas muscle.

19. The method of claim 18, wherein the nerve monitoring is used to position the initial dilator as posterior as possible while remaining anterior to the nerve.

20. The method of claim 19, wherein the plurality of blades includes a posterior blade and comprising the additional step of fixing the position of the posterior blade just anterior to the nerve prior to adjusting to the second configuration such that adjusting to the second configuration comprises moving at least one of the plurality of blades away from the posterior blade.

* * * * *